United States Patent [19]

Barsne

[11] Patent Number: 5,658,326
[45] Date of Patent: Aug. 19, 1997

[54] PROTECTIVE BODY FOR AN IMPLANTABLE ELECTRICAL CONDUCTOR AND AN ELECTRICAL CONDUCTOR EQUIPPED WITH SUCH AN END PROTECTOR

[75] Inventor: Mans Barsne, Stockholm, Sweden

[73] Assignee: Pacesetter AB, Solna, Sweden

[21] Appl. No.: 705,273

[22] Filed: Aug. 29, 1996

[30] Foreign Application Priority Data

Sep. 12, 1995 [SE] Sweden .................. 9503144

[51] Int. Cl.⁶ .................................. A61N 1/05
[52] U.S. Cl. .................................. 607/126
[58] Field of Search .................. 128/642; 607/116, 607/126, 127, 128, 130, 131

[56] References Cited

U.S. PATENT DOCUMENTS

| | | |
|---|---|---|
| 3,974,834 | 8/1976 | Kane . |
| 4,106,512 | 8/1978 | Bisping . |
| 4,311,153 | 1/1982 | Smits . |
| 4,827,940 | 5/1989 | Mayer et al. . |
| 4,876,109 | 10/1989 | Mayer et al. . |
| 5,531,783 | 7/1996 | Giele et al. ............ 607/126 |

FOREIGN PATENT DOCUMENTS 908373   2/1982   U.S.S.R. ............ 607/128

Primary Examiner—William E. Kamm
Assistant Examiner—George R. Evanisko
Attorney, Agent, or Firm—Hill, Steadman & Simpson

[57] ABSTRACT

A device for preventing a fixation element on the distal end of an implantable lead, during introduction into a body cavity, from coming into contact with and damaging the cavity has a protective body, which completely encloses the fixation element, and which is made of a gel-forming material. After introduction and contact with body fluid and when pressure is applied to the material against body tissue, the material permits mechanical penetration of the protective body by the fixation element, whereupon the fixation element can be affixed to the body cavity.

14 Claims, 1 Drawing Sheet

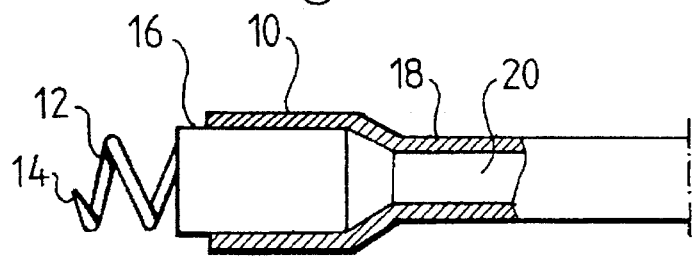
Fig. 1
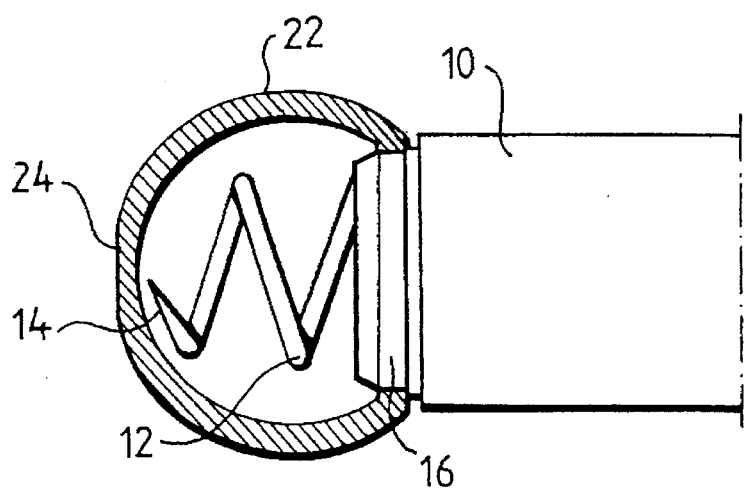
Fig. 2
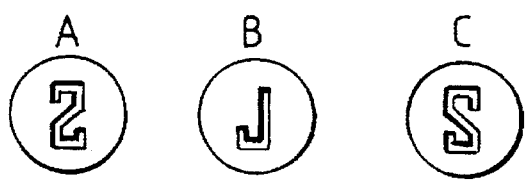
Fig. 3
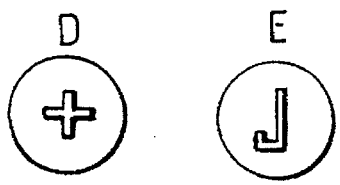

स,658,326

PROTECTIVE BODY FOR AN IMPLANTABLE ELECTRICAL CONDUCTOR AND AN ELECTRICAL CONDUCTOR EQUIPPED WITH SUCH AN END PROTECTOR

BACKGROUND OF THE INVENTION

1. Field of the Invention

The present invention relates to a protective body to keep a fixing element on the distal end of an implantable lead from coming into contact with and damaging the walls of a body cavity during introduction of the lead into the cavity, the protective body being of the type formed by a covering of a material which, following introduction and contact with body fluid, and when pressure is applied to the material against body tissue, allows mechanical penetration of the protective body by the fixing element enabling the fixing element to be anchored in the body cavity.

2. Description of the Prior Art

An implantable lead, i.e. an electrode cable, intended for connection at one end, the proximal end, to a medical device, such as a pacemaker, and whose other end, the distal end, is to be affixed in a ventricle or atrium of the heart, can be passively or actively affixed to the heart wall, after intravenous introduction into the heart, in order to transmit electrical pulses to heart muscle, thereby inducing this tissue to contract, or to sense the heart's intrinsic activity in control of the pacemaker's operating cycle. For passive fixing of the distal end of the lead, this lead end is usually equipped with small tines or barbs to facilitate anchoring in the heart wall without penetrating the heart wall.

In order to achieve rapid, reliable fixing of the distal end of the lead to the heart wall, e.g. when the end of the lead is to have a J shape and press against an atrial wall, active fixing of the end to the atrial wall is preferred. For this purpose, the end of the lead has a fixing element which can be driven into wall tissue in implantation, a process which can be monitored by fluoroscopy to ensure that the end of the lead is correctly positioned.

A commonly used fixing element for this purpose has the shape of a pointed, helical screw. Such lead ends are screw-in types and require active insertion of the fixing element into the heart wall. In cases where the helical screw can freely rotate on the end of the lead, the helical screw can be rotated with the aid of a stylet which is inserted from the proximal end of the electrode cable and made to grip a polygonal recess in the proximal end of the helical screw, the screw then being screwed into and affixed to the heart wall with the end of the electrode pressing against the wall.

In order to keep the pointed tip of the helical screw from coming into contact with and damaging venous and heart walls during the implantation of the lead, the aforementioned freely rotating helical screw can initially be retracted inside a protective recess in the end of the lead and can be deployed by the stylet only after it arrives at the intended implantation site, just before the helical screw is screwed in.

Another type of fixing element for active fixing of the end of the lead to the heart wall has, on the distal end of the lead, a non-rotating helical screw which projects from that end. In this instance, the helical screw must be provided with some kind of protection to keep the tip of the helical screw from damaging venous and heart walls during the implantation of the lead. The entire lead, including its covering, must then be rotated in order to screw the helical screw into the heart wall.

A number of different solutions have been proposed for preventing such projecting, non-rotating helical screw from causing damage during introduction. One proposal is described in U.S. Pat. No. 3,974,834 in which a compressible, bellows-like sleeve on the distal end of the lead protects the helical screw during intravenous introduction of the lead, an dis compressed when pressed against the heart wall, so the tip of the helical screw can get a foothold before being screwed into the heart wall.

The solution according to U.S. Pat. No. 3,974,834 has some disadvantages. A relatively large amount of foreign material is introduced into the heart, thereby imposing a load on the heart wall. In some patients, this can disrupt heart activity. In addition, the bellows-like sleeve is not mechanically locked during intravenous introduction This means that the helical screw could be exposed prematurely and inflict damage on vessels and the heart during careless introduction.

U.S. Pat. Nos. 4,827,940 and 4,876,109 disclose relatively hard bodies made of a water-soluble substance, such as mannitol, which covers the helical screw and which dissolves in body fluids within a few minutes, whereupon the helical can be screwed into the heart wall. As long as a body according to any of these documents remains in place, the helical screw covered by the body cannot damage vessels or the heart.

The protective bodies described in U.S. Pat. Nos. 4,827,940 and 4,876,109 dissolve rather rapidly in blood, and the helical screw means is exposed in 2–4 minutes. Experiences physicians might regard this dissolution time as long, and their inability to govern this time themselves is unsatisfactory to many. Inexperienced physicians, on the other hand, may view this dissolution time as brief, causing them to feel stressed.

U.S. Pat. Nos. 4,106,512 and 4,311,153 each disclosed leads equipped with protective bodies made of silicon rubber. In contrast to the protective bodies of the previously cited patents, the silicon rubber bodies are insoluble in body fluids. Hence, the silicon rubber bodies will remain in the heart after the lead has been affixed to the heart wall, and it is just as easy for the helical screw to penetrate the protective body when the lead enters the body as it is just before the lead is to be affixed to the heart.

Consequently there is a need for a new type of small, simple protective body for covering the helical screw on a pacemaker lead with the aid of which controlled exposure of the electrode's helical screw is possible immediately before the screw is screwed into the heart wall.

SUMMARY OF THE INVENTION

It is an object of the present invention to provide a protective body for covering the helical screw, serving as a fixing element, of a pacemaker lead which permits a controlled exposure of the helical screw immediately before the screw is screwed into the heart wall.

The above object is achieved in accordance with the principles of the present invention in a protective body which completely encloses the fixing element at the distal end of an implantable electrical conductor, the protective body preventing the fixing element, during introduction of the conductor into a body cavity, from coming into contact with and damaging the cavity, and the protective body comprising a gel-forming material which, after introduction to and contact with body fluid and after pressure is applied to the material against body tissue, permits mechanical penetration of the fixing element through the protective body, thereby enabling the fixing element to be affixed to the body cavity.

Examples of gel-forming materials which can be used in conjunction with the invention are gelatin-based materials and cross-linked, synthetic hydrophillic polymers, such as cross-linked polyethylene glycol (PEG), cross-linked cellulose and cellulose derivatives, dextran etc. Gelatin-based materials are used in one particularly preferred embodiment of the invention.

Gelatin is a protein material made from animal hides, tendons, bone tissue etc. It mainly consists of hydrolyzed collagen. Collagen is found in all animals, including Man, and is the basis of fibrous tissue.

Gelatin has many properties which are useful in conjunction with implant materials. It is biodegradable and is also a natural substance found in the body. This means that it does not trigger undesirable immune responses, pathological conditions or intoxication. Gelatin has an ability to form heat-reversible gels in water. These gels are stable at rom temperature. At temperatures close to body temperature, these gels slowly swell and become more fragile. They dissolve at higher temperatures. A new gel forms when the temperature is reduced.

The material hardens and loses its gel character when the water content of the gelatin is reduced. It shrinks but simultaneously acquires an ability to resist external mechanical force.

Modification of gelatin with cross-linking substances, such as formaldehyde, glyoxal or glutaraldehyde, can stabilize the gel structure. A person skilled in the art can control the gel's properties by varying the amount of cross-linking additives.

DESCRIPTION OF THE DRAWINGS

FIG. 1 shows a lateral, cross-sectional view of the distal end of a known implantable lead without any protection for the helical screw.

FIG. 2 shows a cross-sectional view of the distal end of an implantable lead whose helical screw element is protected by a body made of gel-forming material according to the invention.

FIGS. 3A–3E show different examples of protective body patterns in the form of raised portions and depressions.

DESCRIPTION OF THE PREFERRED EMBODIMENTS

FIG. 1 shows an example of the distal end section 10 of a lead which is intended for active fixing to a cavity in the heart. The end section 10 is equipped with a helical screw 12 with a sharp tip at its outermost end. The helical screw 12 is attached to a cylindrical metal carrier 16 which is in electrical contact with an electrical conductor 20. The conductor 20 is surrounded by a sleeve 18 made of an electrically insulating material.

In FIG. 2, the distal end section 10 in FIG. 1 has been equipped with a protective body 22 made from a gel-forming material according to the invention. The external, forward end of the body 22 opposite the tip 14 has a pattern 24 to provide some torsional resistance when the electrode is to be affixed to the heart wall.

FIGS. 3A–3E show examples of different patterns 24. The pattern can be designed as depressions or recesses (FIGS. 3A–3C) or raised portions (FIGS. 3D–3E) in the gel-based material. According to one embodiment of the invention, the pattern is devices so that torque is greater for rotation in one direction than for rotation in the opposite direction (FIGS. 3B, 3E).

As previously noted, the use of a gelatin-based material as the gel-forming material is particularly preferred. The type of gelatin employed in conjunction with this embodiment is not a critical parameter, and the invention can be realized with many different kinds of gelatin. Gelatin types with a high molecular weight generally dissolve more slowly. Slower dissolution, better gel stability and a drier, solid form can be achieved by cross-linking the gelatin with, e.g., formaldehyde, glyoxal or glutaraldehyde. Hence, the dissolution time can be varied within a wide range and is normally within a range from 1 hour to 1 week, preferably from 24 hours to one week, which is a much longer time than in the prior art according to U.S. Pat. Nos. 4,827,940 and 4,876,109. A person skilled in the art can easily select a suitable kind of gelatin for a particular application.

The protective body 22 of gelatin can be attached to the end 10 of the lead in a number of different ways. The end section 10 with the helical screw 12 can be dipped into lightly heated gelatin solution. After this immersion, gelatin deposited on the helical screw 12 is allowed to harden. If the gelatin coating is deemed to be too thin, the helical screw 12 is dipped into the gelatin solution again. The procedure is repeated until the thickness of the gelatin coating 22 is satisfactory. The temperature of the gelatin solution is kept somewhat higher than the temperature at which the type of gelatin hardens, e.g., 40°–50° C. for a type of gelatin which hardens at a temperature just under 40° C. The concentration of the gelatin solution is within a range from 0.5 to 40%, preferably from 2 to 20%.

The protective body 22 can also be made of cast gelatin. A gelatin solution at a temperature just above the temperature at which the used gelatin type hardens, e.g., 40° to 55° C., is poured into an appropriate mold. In this procedure, the gelatin solution's concentration is higher than the concentration of a solution suitable for immersion coating and is in a range from 3 to 50%, preferably from 10 to 40%, and from 20 to 35% in particular. The distal end section 10 can be placed in the mold in conjunction with the molding of the gelatin. When the gelatin hardens, the protective body 22 adheres to the end section 10. Alternatively, the protective body 22 can be cast separately and then applied to the end section 10. Gelatin solution can be injection molded when the protective body 22 is made.

After fabrication, the protective gelatin body 22 is dried, whereupon the gelatin's gel character disappears, and the material hardens. The electrode cable is packaged after visual inspection of the protected end section 10.

Sterilization of the lead with a protected end 10 can be performed in different ways. The electrode cable, with the protective gelatin body in place, can be sterilized either with radiation, or the cable can be sterilized separately in a suitable manner familiar to those skilled in the art. The gelatin in the form of a solution is subjected to sterile filtration, and the protective body 22 is applied in a sterile environment in one of the ways described above.

Preventing the protective gelatin body 22 from drying too much during storage is important. Excessive drying could lead to deformation of the enclosed helical screw 12 when the pressure of the gelatin body 22 on it increases or the expansion capability of the gelatin body during re-hydration could be irreversibly impaired.

This problem can be solved by including material, moistened with water, in the package. A salt, such as sodium chloride or a hydrophilic polymer, such as polyethylene glycol, can be added to the gelatin solution during fabrication of the protective gelatin body 22. Sodium chloride loosens the gelatin's structure, whereas the polyethylene glycol makes the protective gelatin body 22 more hygroscopic.

When the lead having a protective body end protection is implanted, the protective gelatin body 22 is re-hydrated. The body 22 then swells and becomes fragile. When the implantable electrode cable is inserted a sufficient distance into the heart, the helical screw 12 is exposed when the protective end section 10 is pressed, and possibly twisted, against an appropriate site on the endocardium. A pattern 24, in the form of depressions and/or raised areas or ridges, on the gelatin body 22 contributes to increase torsional resistance and, accordingly, penetration of the protective gelatin body 22. According to one embodiment of the invention, the pattern 24 can be devised in such a way that resistance is greater for rotation in one direction than for rotation in the opposite direction. The protective gelatin body 22 then splits and is forced down to form a collar around the cylindrical metal carrier 16, whereupon the helical screw 12 penetrates the endocardium. The gelatin ultimately dissolves and is absorbed.

The invention is further illustrated by the following embodiment:

EXAMPLE

The distal end 10 of an implantable lead, intended for use with a pacemaker and whose end is equipped with a helical screw 12, was dipped into a 10% solution of nor-mal food-grade gelatin (Törsleff AB, Ekerö). The temperature of the solution was 41' C. The end 10 of the electrode was immersed far enough to completely cover the helical screw 12 and the cylindrical metal carrier 16. The duration of immersion was 5 seconds, whereupon the adhering gelatin solution was allowed to harden for 2 minutes. The immersion procedure was repeated 10 times. The gelatin-covered end was then dried at room temperature for 24 hours. By then the gelatin had lost its gel character. Its strength was checked by pressing a metal wire against the layer of gelatin. The gelatin withstood the pressure, showing that gelatin strength was satisfactory. The gelatin-coated end 10 was then immersed in water with a temperature of 37° C. The gelatin swelled and could be perforated by the metal wire.

Although modifications and changes may be suggested by those skilled in the art, it is the intention of the inventors to embody within the patent warranted hereon all changes and modifications as reasonably and properly come within the scope of their contribution to the art.

I claim as my invention:

1. A protective arrangement for use with an implantable medical electrical conductor having a distal end with a fixing element disposed at said distal end, said distal end of said implantable medical electrode conductor being introducible into a body cavity, said protective arrangement comprising:

a protective body completely enclosing said fixing element and preventing said fixing element, during introduction of said conductor into said body cavity, from coming into contact with and damaging said cavity; and said protective body being composed of a gel-forming material which, after introduction and contact with body fluid and after application of pressure to said gel-forming material against body tissue, permits mechanical penetration by said fixing element through said protective body for enabling said fixing element to become affixed to the body cavity.

2. A protective arrangement as claimed in claim 1 wherein said protective body comprises a gel-forming material which is mechanically penetrable when pressed against an endocardium as said body cavity.

3. A protective arrangement as claimed in claim 1 wherein said protective body is composed of a gel-forming material selected from the group consisting of gelatin-based materials and cross-linked synthetic hydrophillic polymers.

4. A protective arrangement as claimed in claim 3 wherein said protective body is composed of a gel-forming material consisting of a cross-linked synthetic hydrophillic polymer selected from the group consisting of cross-linked polyethylene glycol, cross-linked cellulose, cross-linked cellulose derivatives, and cross-linked dextran.

5. A protective arrangement as claimed in claim 1 wherein said protective body consists of a gelatin-based material.

6. A protective arrangement as claimed in claim 1 further comprising a pattern disposed on said protective body having raised and lowered portions for increasing a torsional resistance of said protective body.

7. A protective arrangement as claimed in claim 1 wherein said protective body comprises a gelatin-based material formed from gelatin and water.

8. A protective arrangement as claimed in claim 1 wherein said protective body consists of a gelatin-based material formed of cross-linked gelatin.

9. A protective arrangement as claimed in claim 8 wherein said gelatin is cross-linked with a cross-linking material selected from the group consisting of formaldehyde, glyoxal and glutaraldehyde.

10. A protective arrangement as claimed in claim 1 wherein said protective body is formed of a gelatin-based material including at least one of a salt or a hydrophillic polymer.

11. A protective arrangement as claimed in claim 10 wherein said salt comprises sodium chloride.

12. A protective arrangement as claimed in claim 10 wherein said hydrophillic polymer comprises polyethylene glycol.

13. A protective arrangement as claimed in claim 1 wherein said protective body comprises a sleeve having an internal cavity in which said fixing element is contained, said fixing element being disposed in said internal cavity so that said fixing element can come into contact with and mechanically penetrate said protective body only when said protective body is subjected to an external force.

14. A protective arrangement as claimed in claim 1 wherein said protective body is formed of a gelatin-based material and is solid, and wherein said fixing element is disposed inside said protective body and is able to penetrate said protective body only when said protective body is subjected to an external force.

* * * * *